(12) United States Patent
Yang et al.

(10) Patent No.: US 8,111,078 B1
(45) Date of Patent: Feb. 7, 2012

(54) OXIDIZING POWER SENSOR FOR CORROSION MONITORING

(76) Inventors: Xiaodong Sun Yang, San Antonio, TX (US); Lietai Yang, San Antonio, TX (US)

( * ) Notice: Subject to any disclaimer, the term of this patent is extended or adjusted under 35 U.S.C. 154(b) by 278 days.

(21) Appl. No.: 12/583,015

(22) Filed: Aug. 13, 2009

Related U.S. Application Data

(60) Provisional application No. 61/189,297, filed on Aug. 18, 2008.

(51) Int. Cl.
*G01R 27/08* (2006.01)
*G01N 27/26* (2006.01)
*G01N 17/04* (2006.01)

(52) U.S. Cl. ........................ 324/700; 204/404; 205/775.5

(58) Field of Classification Search .................. 324/700; 204/404; 205/775.5
See application file for complete search history.

(56) References Cited

U.S. PATENT DOCUMENTS

| | | | |
|---|---|---|---|
| 3,694,324 A | * | 9/1972 | Seyl .............................. 205/777 |
| 4,056,445 A | * | 11/1977 | Gauntt et al. ............... 205/775.5 |
| 6,683,463 B2 | | 1/2004 | Yang et al. |

OTHER PUBLICATIONS

L. Yang, X. Sun and F. Steward, "An On-Line Electrical Resistance Corrosion Monitor for Studying Flow Assisted Corrosion of Carbon Steel under High-Temperature and High-Pressure Conditions." Corrosion/1999, Paper 459 (Houston, TX: NACE International, 1999).
J.R. Scully, "The Polarization Resistance Method for Determination of Instantaneous Corrosion Rates: A Review," Corrosion/1998, paper No. 304 (Houston, TX: NACE International, 1998).
L. Yang and N. Sridhar, "Coupled Multielectrode Online Corrosion Sensor," Materials Performance, September issue, p. 48, 2003.

* cited by examiner

*Primary Examiner* — Melissa Koval
*Assistant Examiner* — Daniel Miller

(57) ABSTRACT

A method based on the measurement of the oxidation power or the cathodic current density using a corrosion-resistant electrode (noble electrode) to derive the bounding corrosion rates of the corroding metal, which is either a stand-alone electrode or an actual component of an equipment, is disclosed. During the measurement, the potential of the noble electrode is controlled at the corrosion potential of the corroding metal. A modified version the sensor that provides a correction factor for the estimation of the corrosion rate according to the bounding corrosion rate is also disclosed. The correction factor is derived based on the cathodic currents measured for the noble electrode and for the corroding metal at a potential that is significantly lower than the corrosion potential, so that the measured cathodic current density from the corroding metal equals the true cathodic current density on the corroding metal.

16 Claims, 21 Drawing Sheets

OXIDIZING POWER SENSOR FOR CORROSION MONITORING

RELATED PATENT APPLICATION

This application claims the benefit of U.S. Provisional Application No. 61/189,297, filed Aug. 18, 2008, by Xiaodong Sun Yang and Lietai Yang, entitled "Oxidizing Power Sensor for Corrosion Monitoring."

TECHNICAL FIELD OF THE INVENTION

This invention relates to methods for monitoring bounding values and estimating the true values of the corrosion rate for a corroding metal using a sensor that is made of a non-corroding metal and measures the oxidizing power that a corrosive environment may have to cause the corroding metal to corrode, or the cathodic current density that a corrosive environment may provide on the surface of a corroding metal.

BACKGROUND OF THE INVENTION

Low-cost sensors for the quantitative corrosion monitoring of engineering structures and equipment in the fields and industrial processes are highly desirable tools for corrosion engineers and plant operators, to enable them to effectively manage corrosion. These structures and equipment include pipelines (both external and internal), concrete re-enforcements (re-bars), airplanes, vehicles, bridge structures (including suspension cables), and equipment used in oil and gas fields, and chemical or power plants. Many of the structures and equipment are covered with protective coatings, and corrosion only takes place in isolated areas on these coated surfaces. An effect monitoring program requires the deployment of a massive number of sensors installed in critical areas or sensors that provide extensive coverage for large equipment. Another desired requirement for the sensors is the ability to provide the corrosion rate information for the actual equipment. Existing probes, such as electrical resistance (ER) probes [see L. Yang et al., "An On-Line Electrical Resistance Corrosion Monitor for Studying Flow Assisted Corrosion of Carbon Steel under High-Temperature and High-Pressure Conditions." CORROSION/1999, Paper 459 (Houston, Tex.: NACE International, 1999).], for general corrosion, and coupled multielectrode array sensor (CMAS) probes, for localized corrosion (see U.S. Pat. No. 6,683,463), are excellent tools for real-time corrosion monitoring. But the CMAS probes are generally expensive and the ER probe has limited life and requires frequent changes of the sensing element. In addition, the ER probes measure the electrical resistance changes due to the cumulative corrosion-induced metal thinning and, thus, have slow responses. The linear polarization resistance (LPR) method [See J. R. Scully, "The Polarization Resistance Method for Determination of Instantaneous Corrosion Rates: A Review," CORROSION/1998, paper no. 304 (Houston, Tex.: NACE International, 1998).] is another widely used, online method and gives nearly instant quantitative corrosion rates for general corrosion. However, this method is derived on the assumption that the corrosion processes are controlled by activation processes. In cases where the corrosion processes are controlled by both activation and diffusion, the LPR method may not be applicable.

Furthermore, all of the above three methods measure the corrosion rate of the probe sensing element that is made with a metal closely matching the system component to be monitored, in chemical composition and metallurgical conditions. The corrosion rates obtained from these probes are not the corrosion rate of the actual system components.

Non-destructive evaluation methods, such as the ultrasonic method and the electrical resistance field method (called field signature method by some suppliers), have been used to directly monitor the rate of corrosion that takes place on the actual pipe or equipment walls. Because the ultrasonic probe has a relatively low resolution limit (>10 µm), and the electrical resistance field method is based on the ER probe principle, both of these two methods are slow and neither can provide adequate information for day-to-day operations in a plant or a field.

The present invention is related to a method that is low cost and can be employed in large numbers in critical areas for the corrosion surveillance. This method uses a non-corroding sensing element, so that the sensing element itself does not require replacement. This method provides a bounding rate for the corrosion taking place on the actual system components, including those under degraded coatings, buried in soils or embed in concrete. In addition, the present invention provides a calibration method that allows the estimation of the corrosion rate of the actual system components based on the bounding value measurements.

Figure 1:
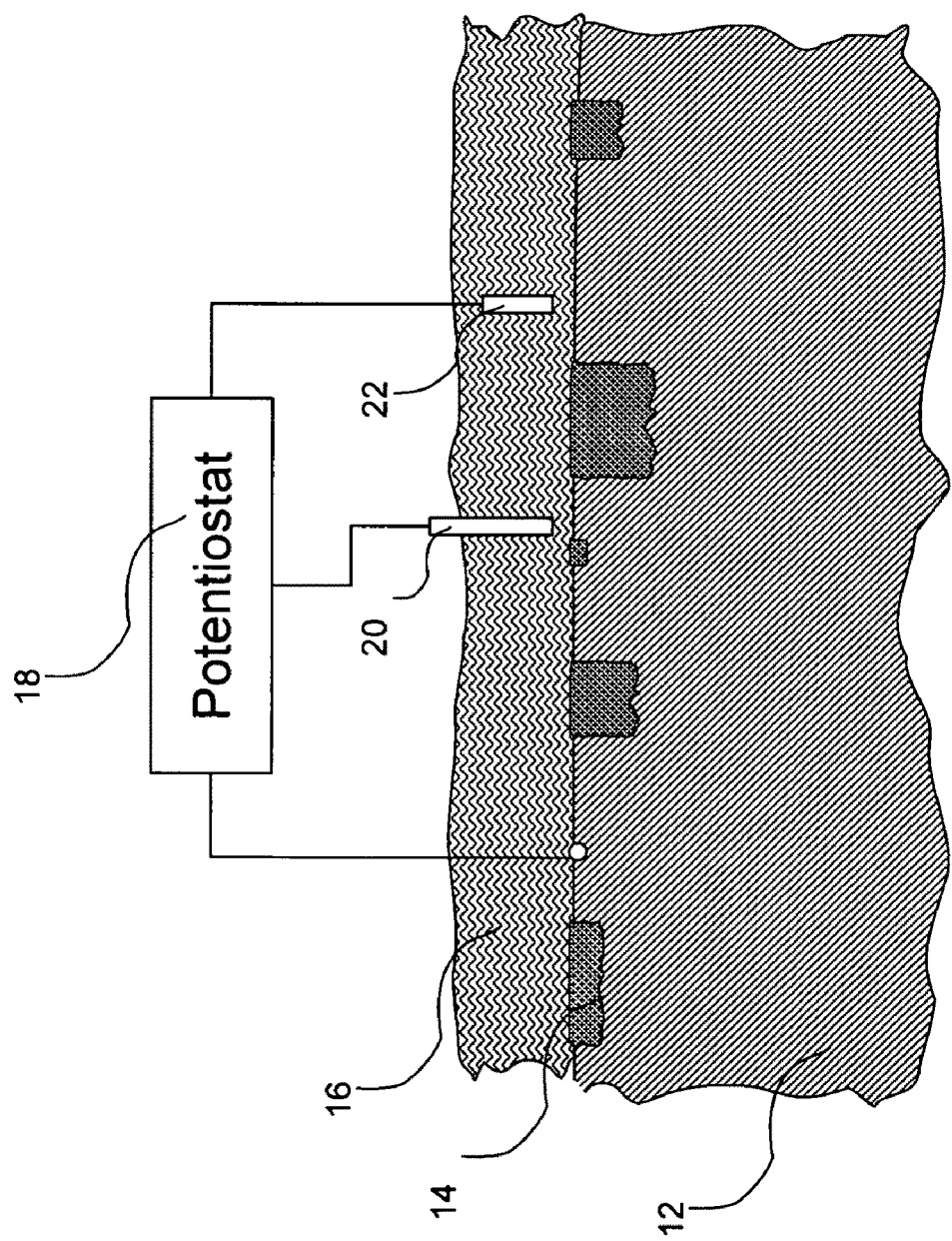
FIG. 1 illustrates a schematic diagram of a maximum oxidation power corrosion sensor.

REFERENCE NUMBERS OF DRAWINGS 12 corroding metal (equipment, structure or coupon)
12a corroding metal electrode
13 additional (second) corroding metal electrode used for measuring reduction current of a corroding metal
14 corroded area (corroded sites or anodic site for localized corrosion)
16 electrolyte (including liquid film, soil, concrete, and any medium supporting ionic conduction)
16a confined electrolyte formed by a solid state electrolyte, a wet sponge, a mop, a water jet, or a water flow
18 potentiostat
20 noble electrode (electrode that does not corrode significantly when held at the potential of the corroding metal; usually made of a corrosion-resistant metal)
20a large noble electrode made of metal wires, strips, or gauze
21 additional (second) noble electrode
22 counter electrode
24 electrical insulator
26 current-measuring devices (including ammeter and zero-resistance ammeter)
26a first current-measuring device
26b second current-measuring device
26c third current-measuring device
30 coating
32 water hose or water jet to form a volume of confined electrolyte
34 voltmeter
36 resistor
38 a voltage source or a battery
40 sacrificial anode to lower the potential of the secondary electrodes (13 & 21)

DETAILED DESCRIPTIONS OF THE INVENTION

Maximum Oxidation Power Corrosion Sensor

Figure 2:
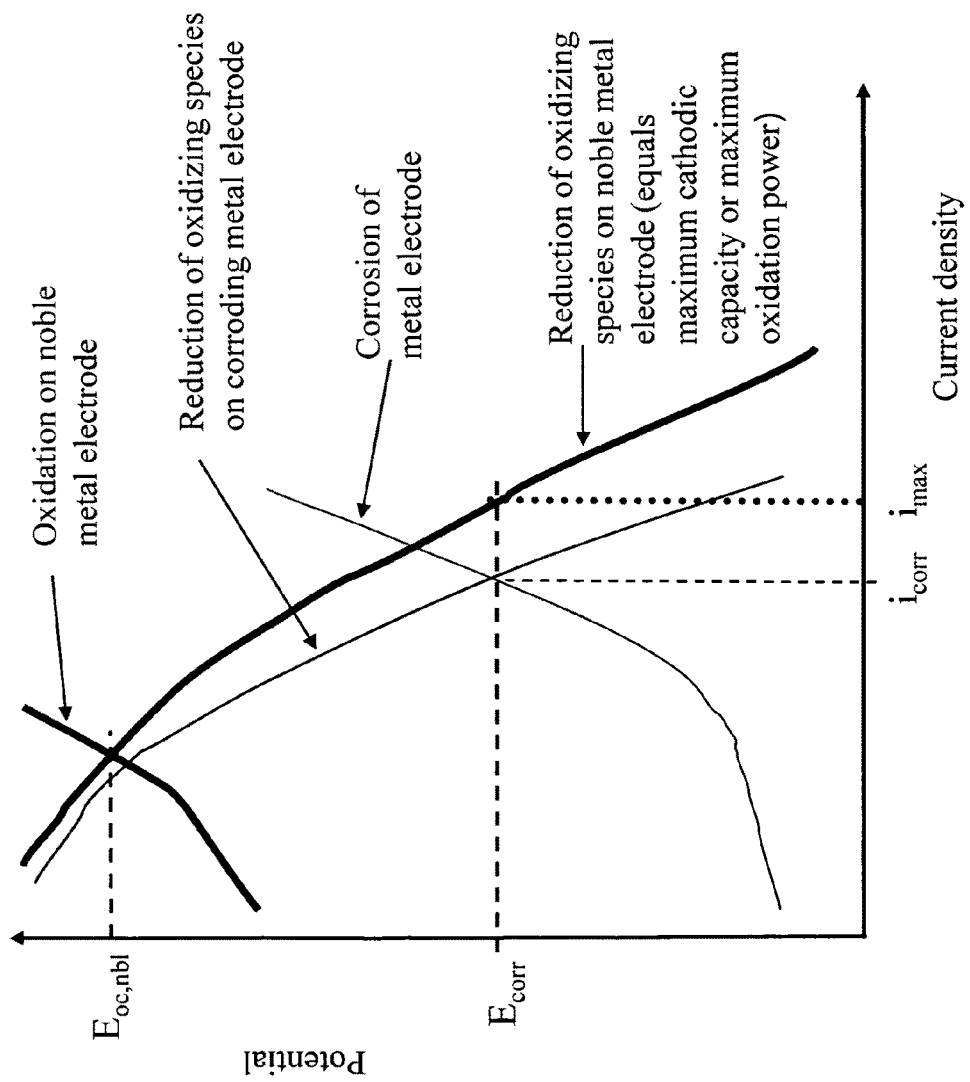
FIG. 2 illustrates the principle of the maximum oxidation power sensor.

FIGS. 1 and 2

FIG. 1 shows the schematic diagram of an oxidation power (OP) corrosion sensor. It has a corroding metal (12) and a noble metal electrode (20), both in contact with an electrolyte (16). The corroding metal has at least one area (14) under corrosion and can be the corroding equipment or structure to be monitored. The noble metal electrode (20) can be of any electrode that is significantly more corrosion-resistant and more catalytically active for the cathodic reactions than the corroding metal. The noble metal electrode is controlled at the same potential as the corroding metal by a potentiostat (18) (or any other means) via a counter electrode (22). The reference electrode connection of the potentiostat is connected to the corroding metal. The cathodic current density from this noble metal electrode is the bounding average corrosion current density (or uniform corrosion current density) for the corroding metal. This cathodic current density is the maximum oxidation power of the electrolyte to cause the metal to corrode on a unit surface area. Detailed explanation is given in FIG. 2:

FIG. 2 shows the principle of the maximum oxidation power sensor. The two thin curves show the reduction current density on a corroding metal electrode caused by the oxidizing species in the electrolyte and the corrosion current density of the corroding metal itself, respectively. When the two curves meet, the potential is equal to the corrosion potential of the corroding metal ($E_{corr}$), and the current density is equal to the corrosion current density ($i_{corr}$). Similarly, the two thick curves show the reduction current density caused by the oxidizing species in the electrolyte and the oxidation current density on the noble metal electrode, respectively. When the two thick curves meet, the potential is the open-circuit potential of the noble metal electrode ($E_{oc,nbl}$). Because the noble metal is selected, such that it is more catalytically active for the reduction reactions of the oxidizing species in the electrolyte, the thick cathodic curve is always on the right of the thin cathodic curve, so that the cathodic current density on the noble metal electrode always bounds the cathodic current density on the corroding metal electrode. In addition, the externally measured reduction current density from the noble electrode equals the reduction current density caused by the oxidizing species in the electrolyte, because the noble metal electrode does not corrode at the corrosion potential (no oxidation current effect, assuming the solution does not contain any other reducing species that can be oxidized on the noble metal electrode at the corrosion potential). For uniform corrosion, the corrosion current density ($i_{corr}$) is equal to the reduction current density on the corroding metal electrode. Therefore, $i_{corr}$ is less or equal to the reduction current density measured on the noble metal electrode ($i_{max}$).

It should be mentioned that the $i_{max}$ obtained from the noble electrode may not be used to bound the localized corrosion current density, because localized corrosion is usually supported by the cathodic current not only from the corroding section, but also from the non-corroding sections. The $i_{corr}$ bounds the corrosion current density averaged over a given surface area of the corroding metal.

Figure 3:
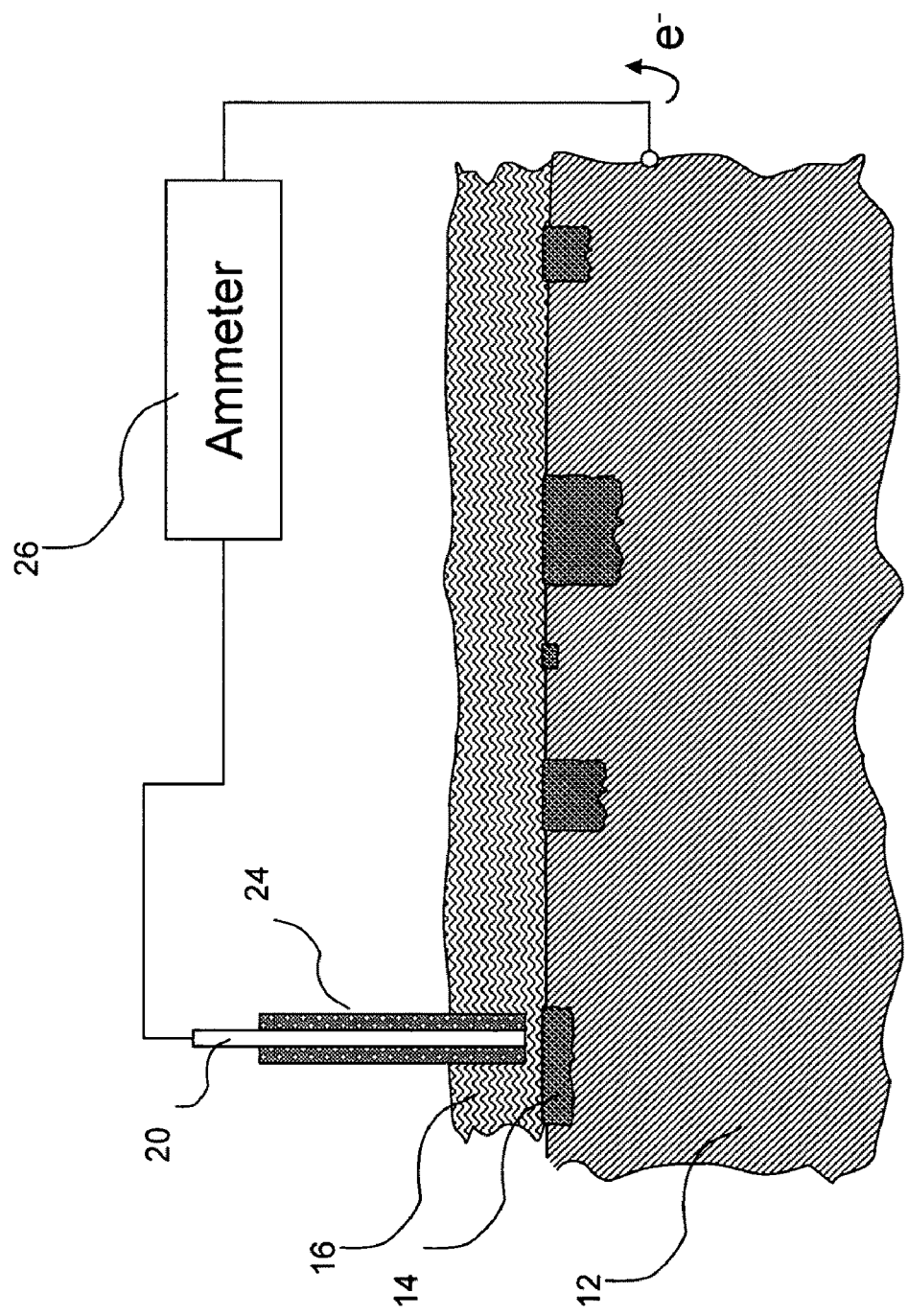
FIG. 3 illustrates a schematic diagram of a maximum oxidation power corrosion sensor formed by coupling the noble electrode to the corroding metal through an ammeter.
Figure 4:
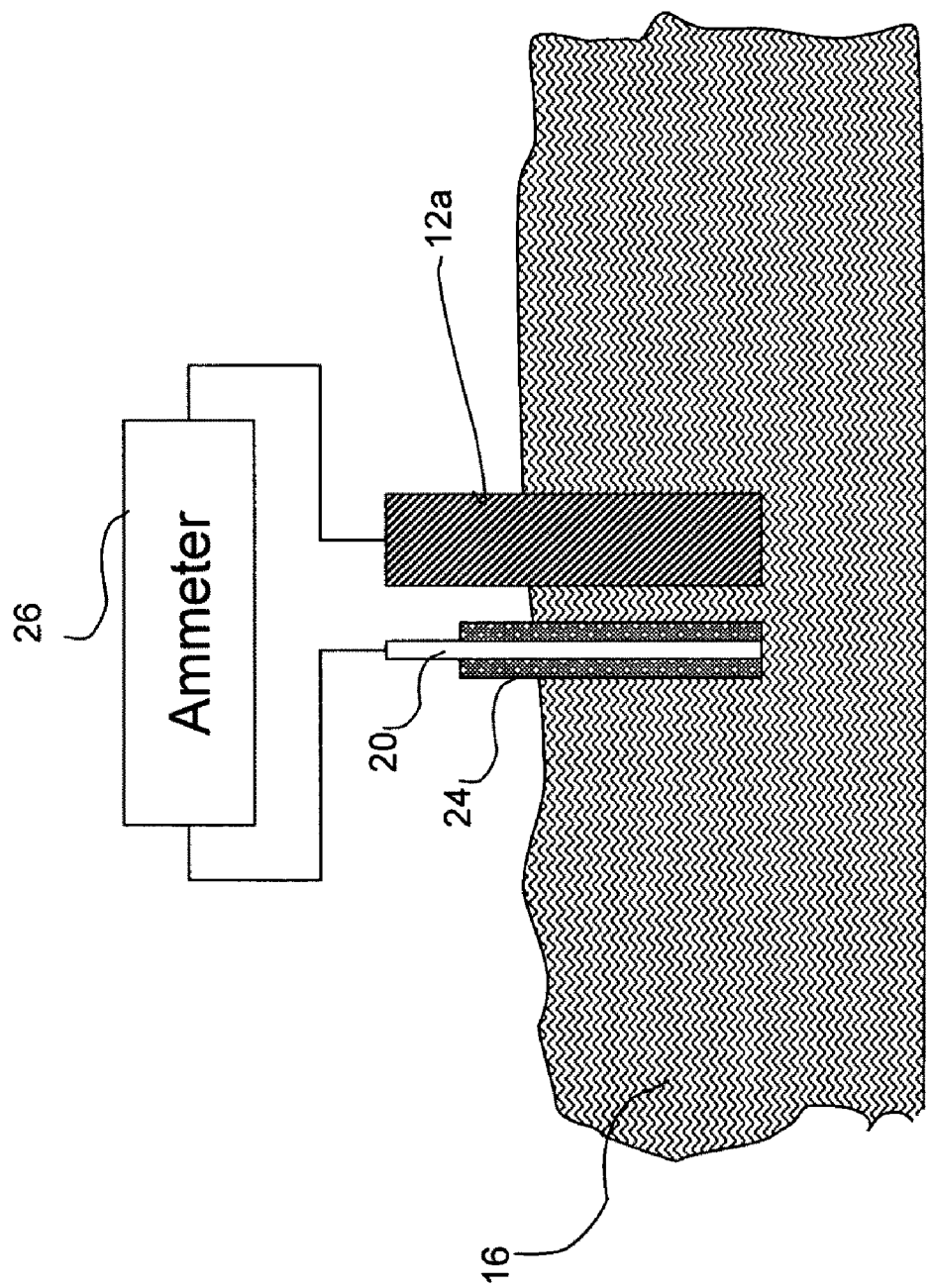
FIG. 4 illustrates a schematic diagram for using a maximum oxidation power corrosion sensor to measure the corrosivity of an electrolyte for a corroding metal.
Figure 5:
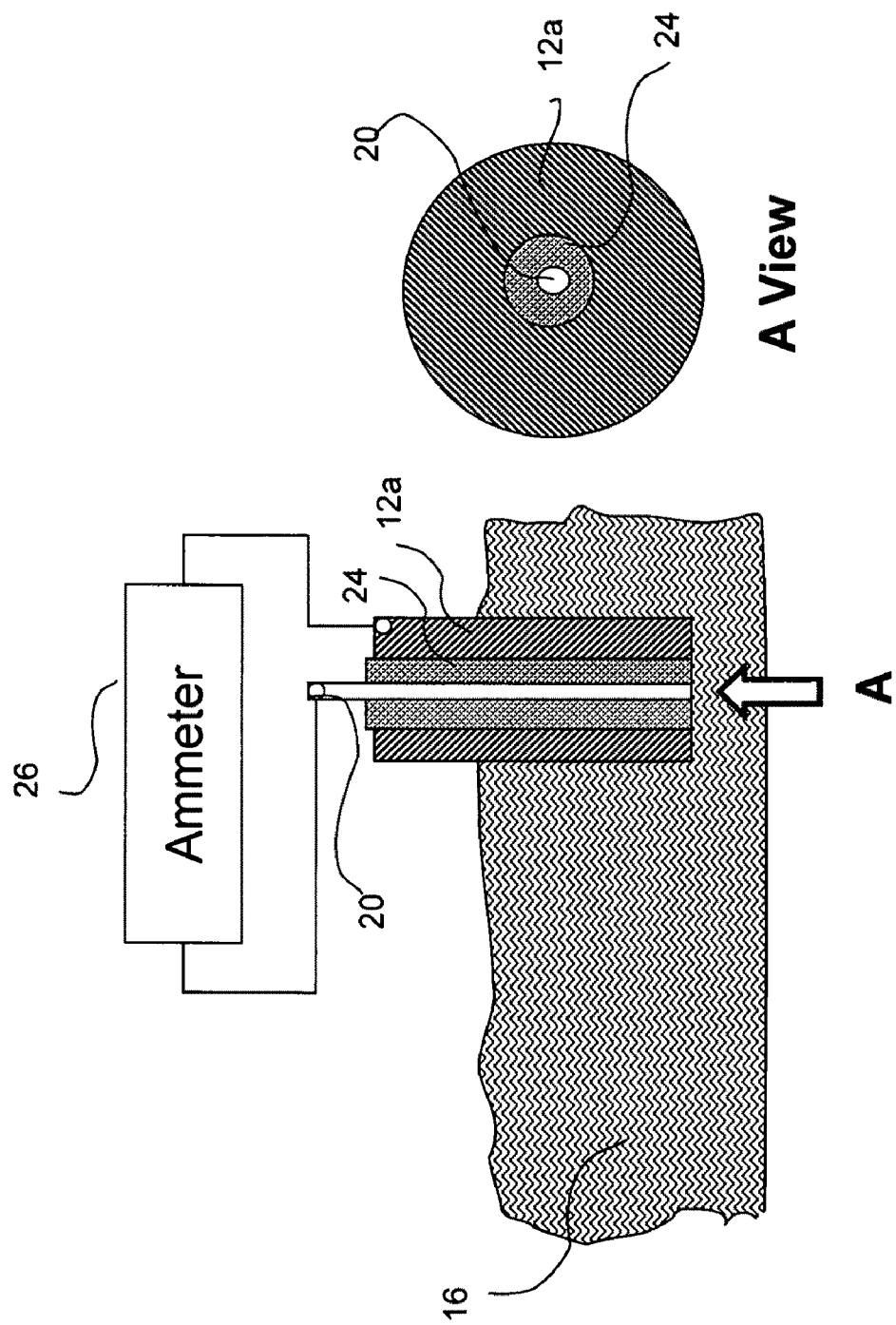
FIG. 5 illustrates a typical compact maximum oxidation power corrosion sensor for measuring the corrosivity of an electrolyte for a corroding metal.

Because the maximum reduction current density that can take place on a corroding metal corresponds to the maximum oxidation power of an electrolyte for the dissolution of the corroding metal, this method is called maximum oxidation power (OP) (or oxidation capacity) corrosion sensor. It may also be called a maximum cathodic current capacity sensor. FIGS. 3, 4 and 5

FIG. 3 shows a typical schematic diagram of a maximum oxidation power corrosion sensor formed by coupling the noble electrode (20) to the corroding metal (12) through a current-measuring device (26), such as an ammeter. The noble electrode surface area is usually sufficiently smaller than that of the corroding metal (usually a large piece of metal equipment). If the ammeter has a near zero potential drop, the noble metal will be at the corrosion potential of the corroding metal. Because the noble electrode is coupled to the corroding metal, such a sensor may also be called a galvanic oxidation power sensor. It should be noted that this type of sensor is fundamentally different from the conventional galvanic sensor, because the conventional galvanic sensor measures the corrosion signal from the corroding metal, while the galvanic oxidation power corrosion sensor measures the corrosion signal (the cathodic current) from the non-corroding electrode.

FIG. 4 shows a typical schematic diagram for using a maximum oxidation power corrosion sensor to measure the corrosivity of an electrolyte (corrosion medium) for a corroding metal. Here, the stand-alone corroding metal electrode, (12*a*) made of the same material as the corroding metal to be monitored, is used to maintain the potential of the noble electrode at the corrosion potential of the corroding metal.

FIG. 5 shows a typical compact maximum oxidation power corrosion sensor for measuring the corrosivity of an electrolyte (corrosion medium) for a corroding metal. The noble electrode is embedded inside the corroding metal, which maintains the potential of the noble electrode at the corrosion potential of the corroding metal, but is electrically isolated from the corroding metal with an electrical insulator (24). FIGS. 6, 7, 8, and 9

Figure 6:
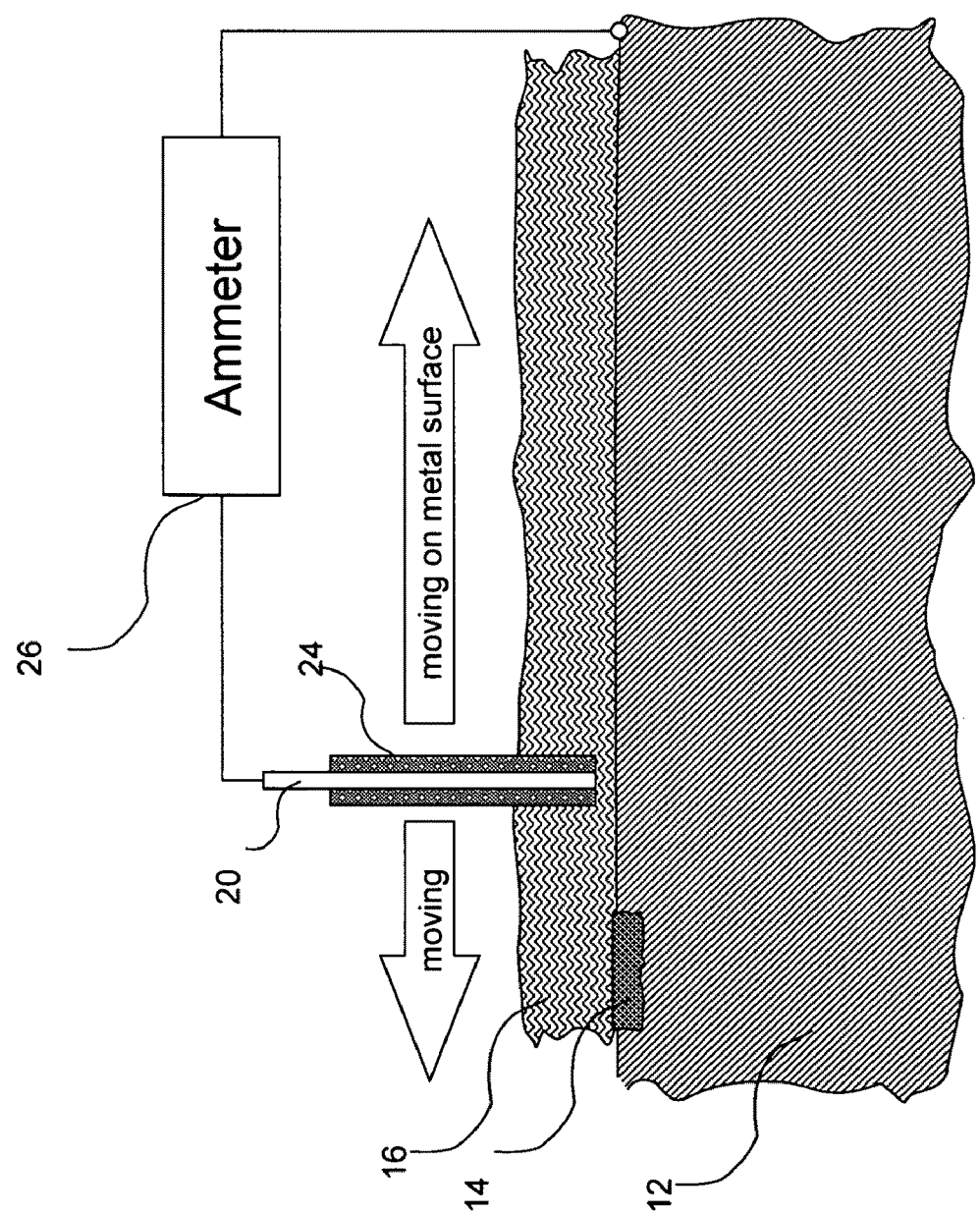
FIG. 6 illustrates a schematic diagram for using a movable (or scanning) maximum oxidation power sensor to detect active corroding areas on a large metal surface in liquid, soil, or concrete.

FIG. 6 shows the schematic diagram for using a movable (or scanning) maximum oxidation power sensor to detect active corroding areas on a large metal surface in liquid, soil, or concrete. When the maximum OP sensor moves closer to the active corroding areas, the coupling current from the noble metal electrode should increase. This is especially true if the electrolyte is thin film liquid, soil or concrete, because of the high electrolyte resistance.

Figure 7:
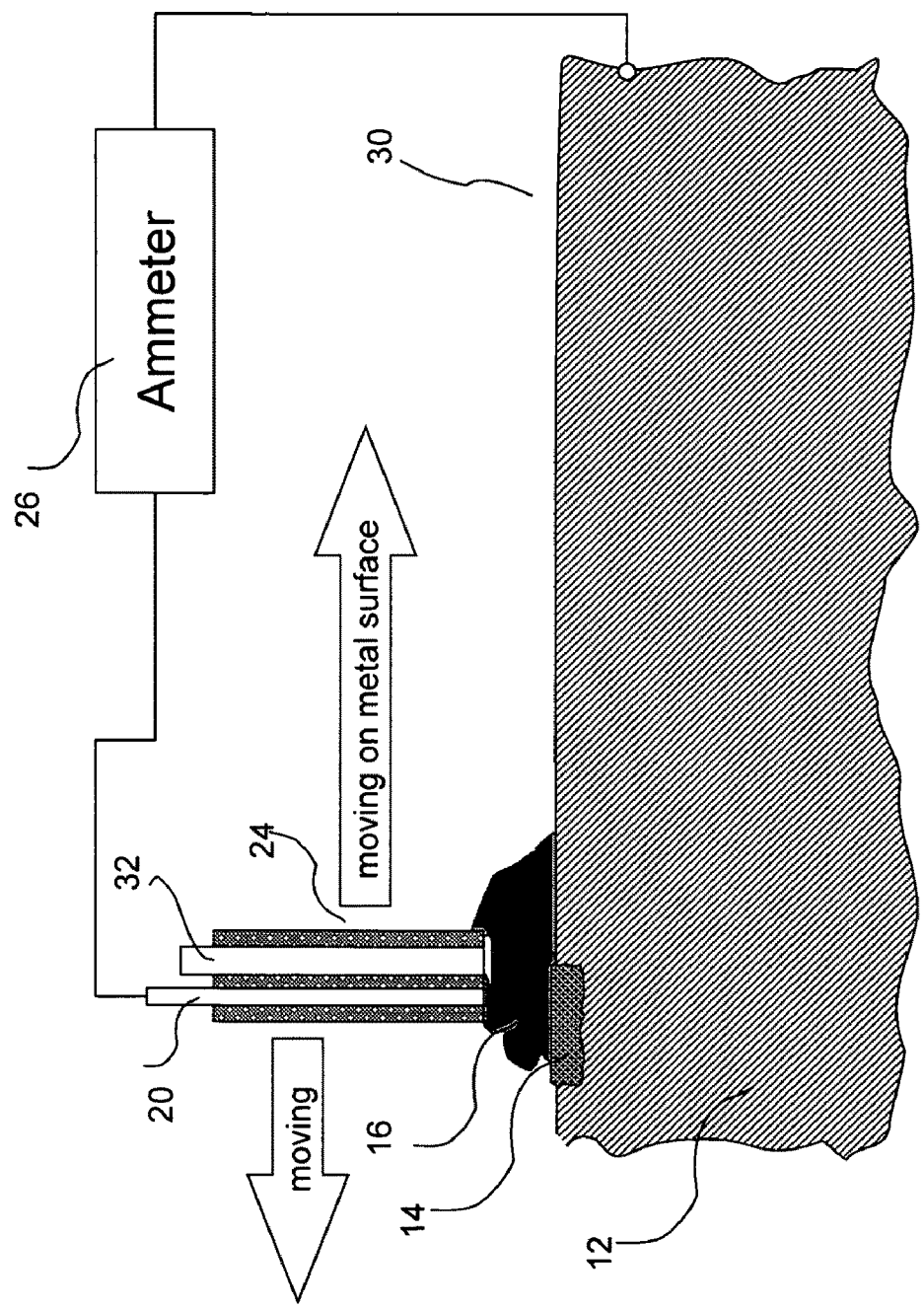
FIG. 7 illustrates a schematic diagram for using a movable maximum oxidation power sensor to detect active corroding areas on a large metal surface exposed to ambient air.

FIG. 7 shows a schematic diagram for using a movable maximum oxidation power sensor to detect the active corroding areas on a large metal surface normally exposed to ambient air. A water hole (32) is incorporated into the sensor that produces a stream or a pocket of electrolyte (16) on the metal surface. This stream of electrolyte forms an ionic conducting path between the noble electrode and the corroding metal.

Figure 8:
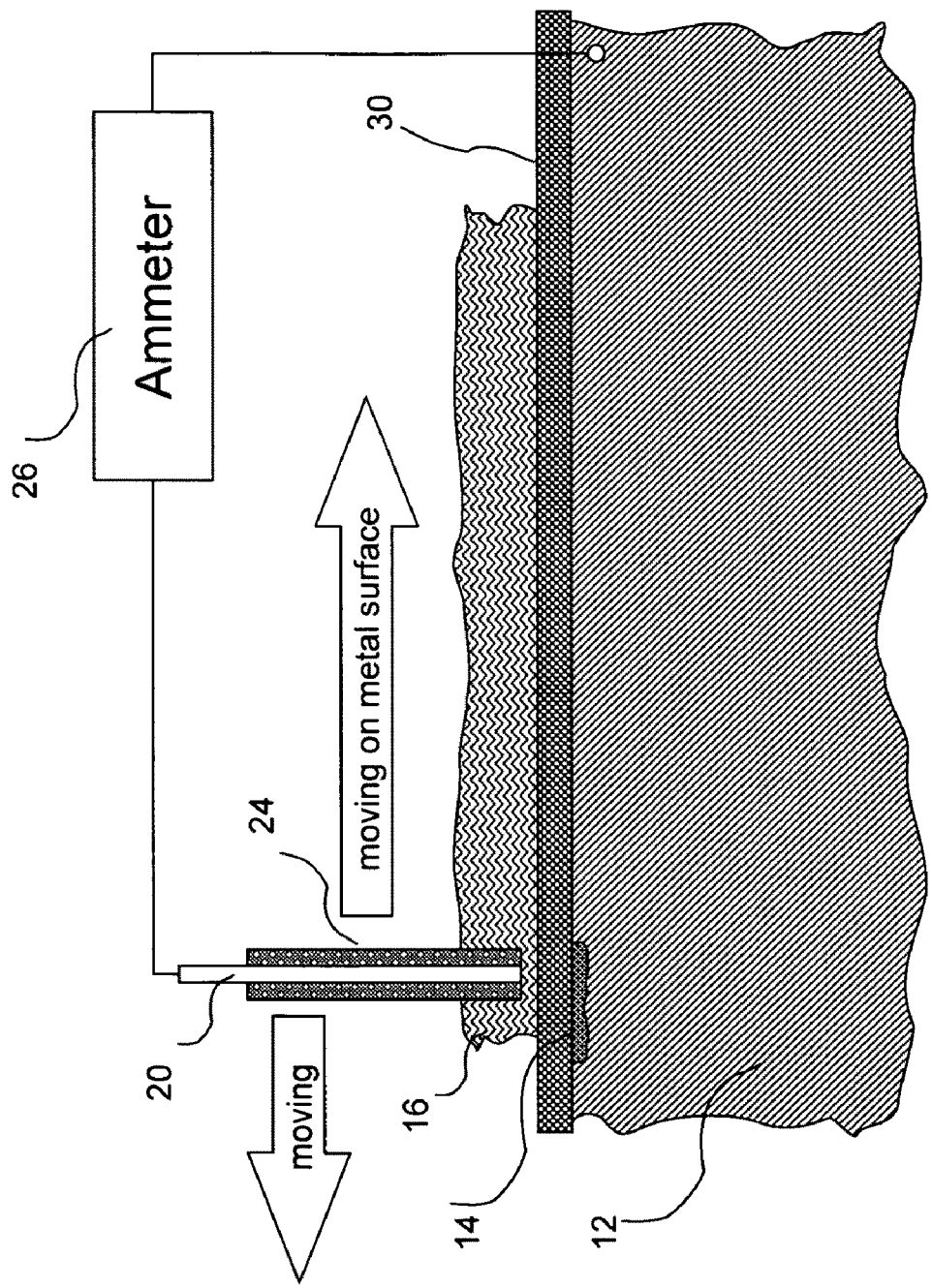
FIG. 8 illustrates a typical schematic diagram for using a movable maximum oxidation power sensor to detect the under coating corrosion of a painted metal surface.

FIG. 8 shows the schematic diagram for using a movable maximum oxidation power sensor to detect corrosion of a metal surface under a coating (30). When the maximum OP sensor moves closer to the corroded areas, the coupling current from the noble metal electrode should increase.

Figure 9:
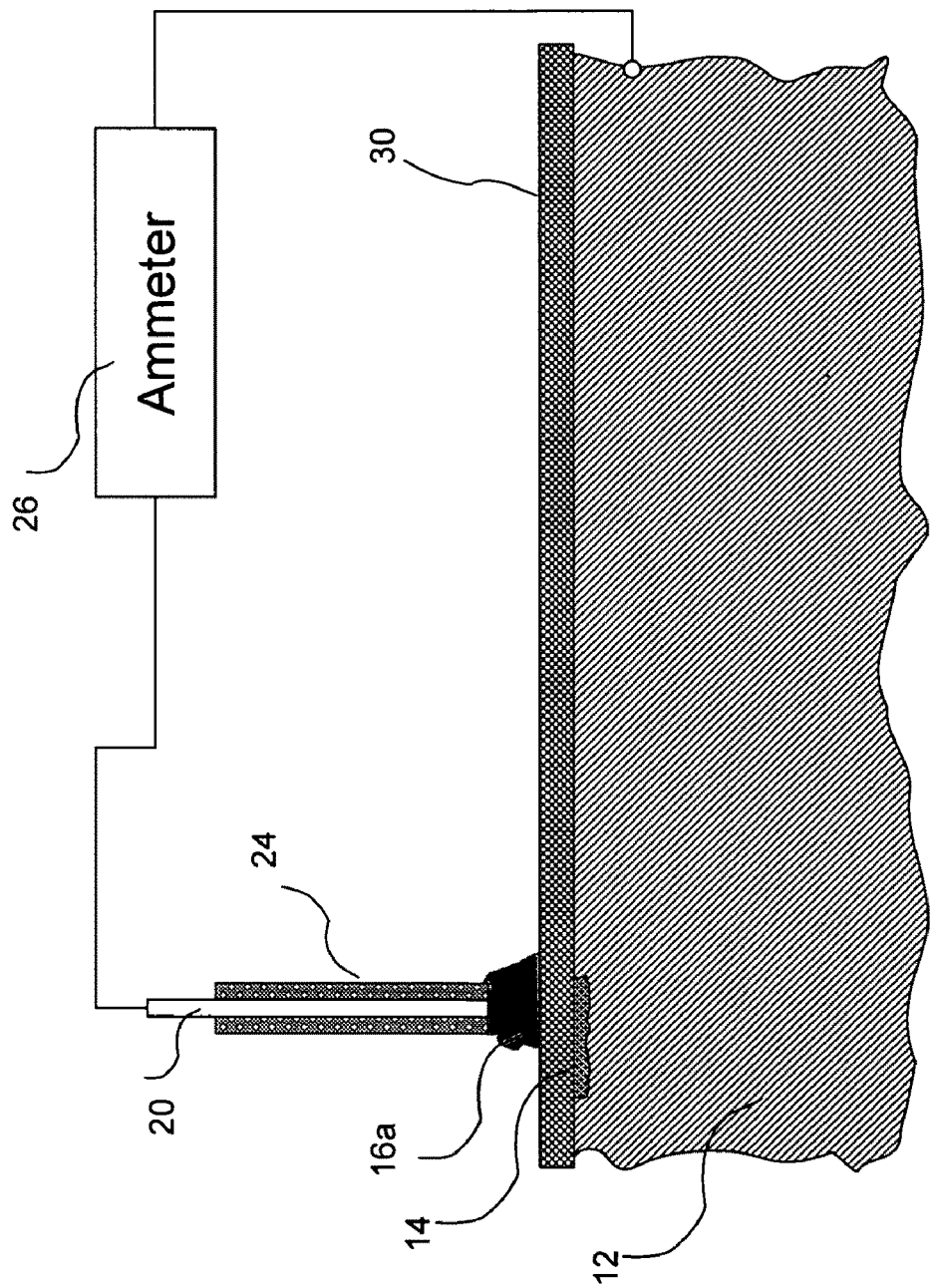
FIG. 9 illustrates the schematic diagram of a maximum oxidation power sensor with a confined electrolyte (formed by a solid polymer electrolyte, or a sponge, wetted cloth, water jet, etc.) at the sensing electrode for corrosion detection of metal components normally exposed in ambient air.

FIG. 9 shows the schematic diagram of the maximum oxidation power sensor with a confined electrolyte (16*a*) (formed by a solid polymer electrolyte, or a sponge, wetted fiber cloth, water jet, or a water flow) at the sensing electrode for corrosion detection of metal components normally exposed to ambient air. The sensor can be easily moved around, and there is no need for an electrolyte to be present on the whole surface of the corroding metal component during the measurement.
FIGS. 10, 11, 12 and 13

Figure 10:
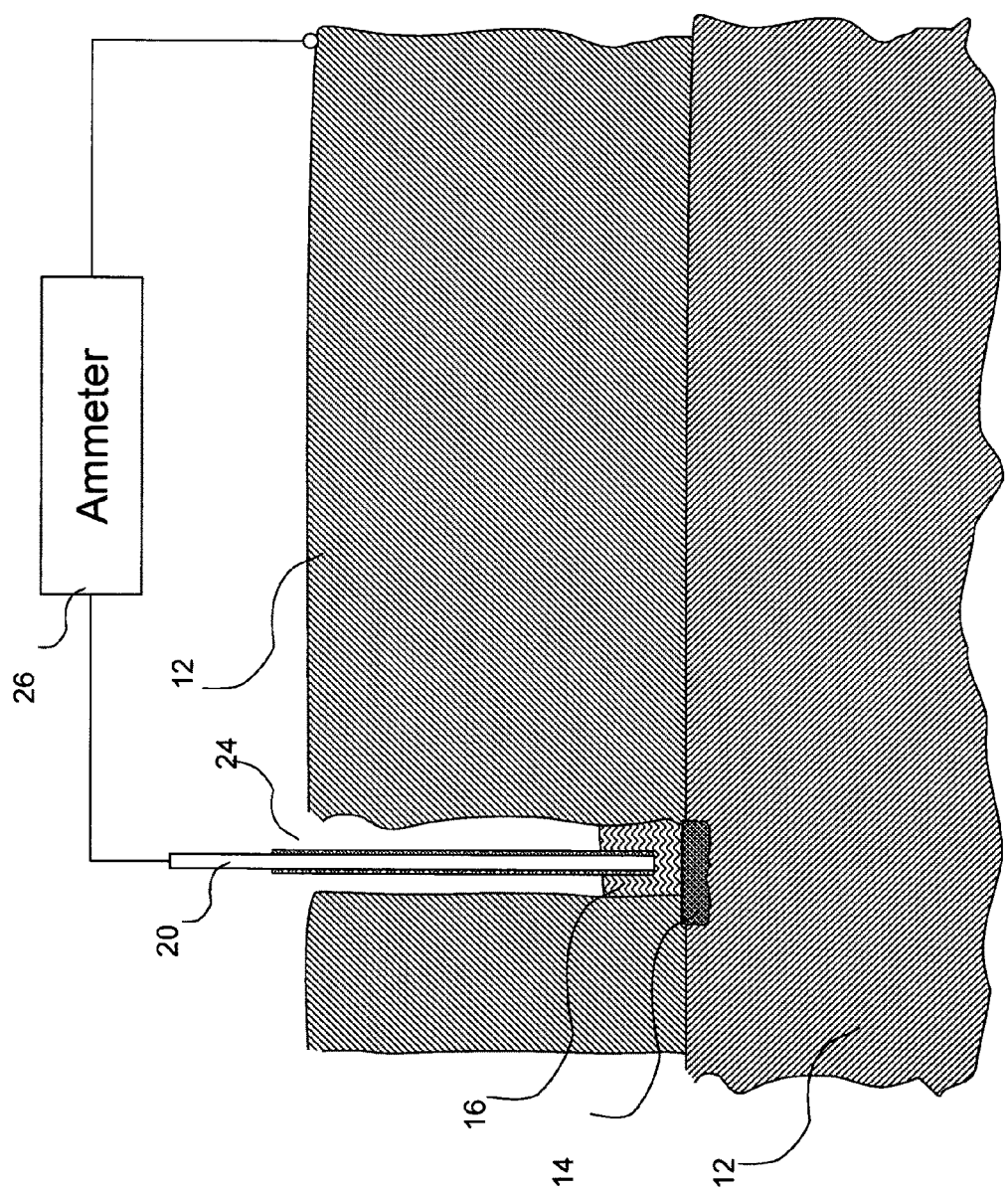
FIG. 10 illustrates a schematic diagram for using a maximum oxidation power sensor to measure corrosion in a hard-to-reach location.

Because the sensing part of a maximum oxidation power sensor consists of a small noble metal electrode, it can be made into any shape and length that may be required to measure the corrosion in hard-to-reach areas. FIG. 10 shows a schematic diagram for using a maximum oxidation power sensor for such applications.

Figure 11:
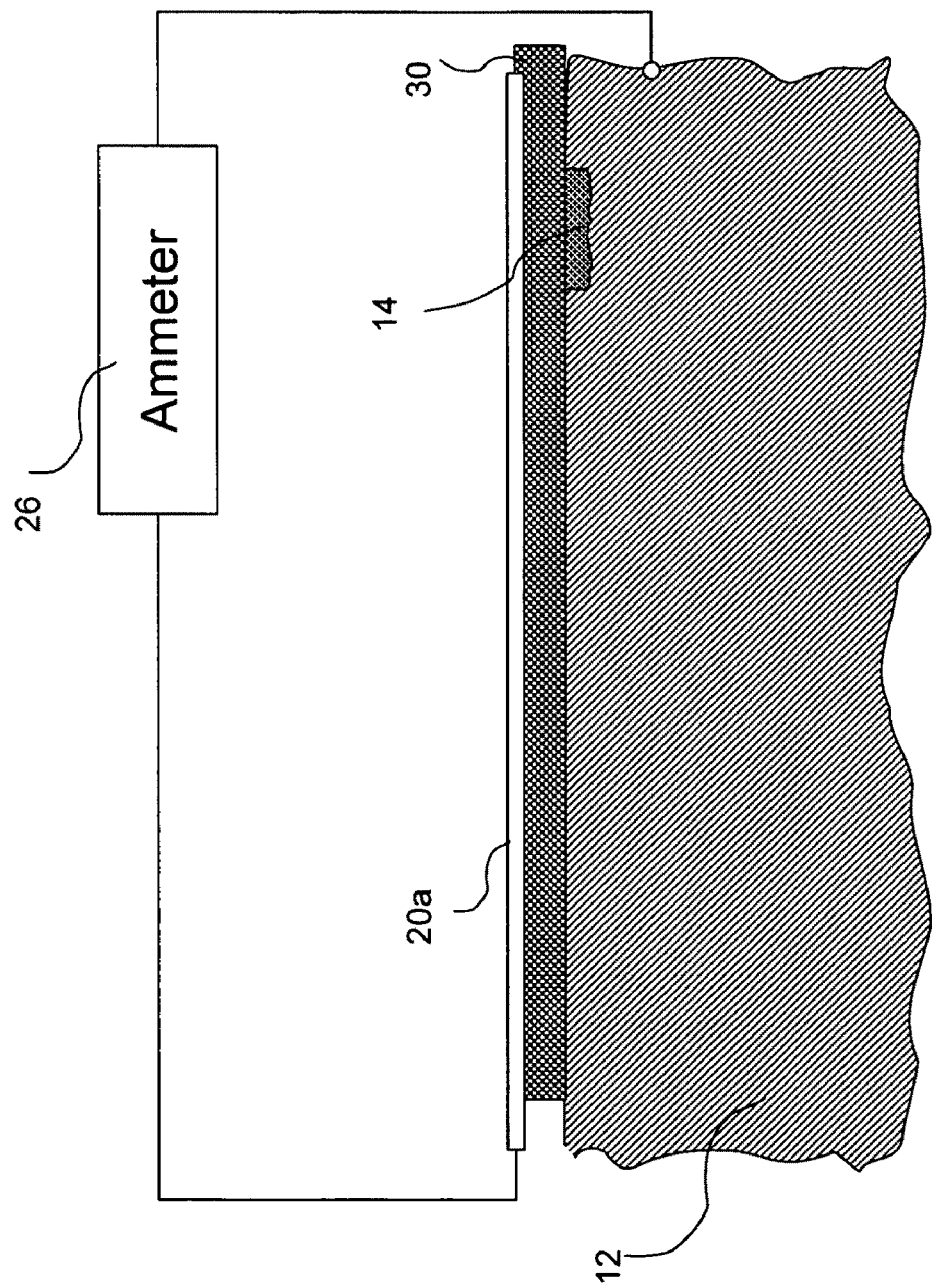
FIG. 11 illustrates a schematic diagram for maximum oxidation power sensor with long and thin noble electrodes attached to the surface of protective coating for corrosion monitoring of undercoating corrosion over large areas.

FIG. 11 shows a schematic diagram for the maximum oxidation power sensor with long and thin noble electrodes (20*a*) attached to the surface of a protective coating for corrosion monitoring of undercoating corrosion over large areas. The long electrodes (thin wires) may be wrapped around a painted pipe immersed in water, buried in soil, or covered by thin water film formed by condensation, rain or fog. The long and thin electrode may be made of wires, foil strips, or metal gauze.

Figure 12:
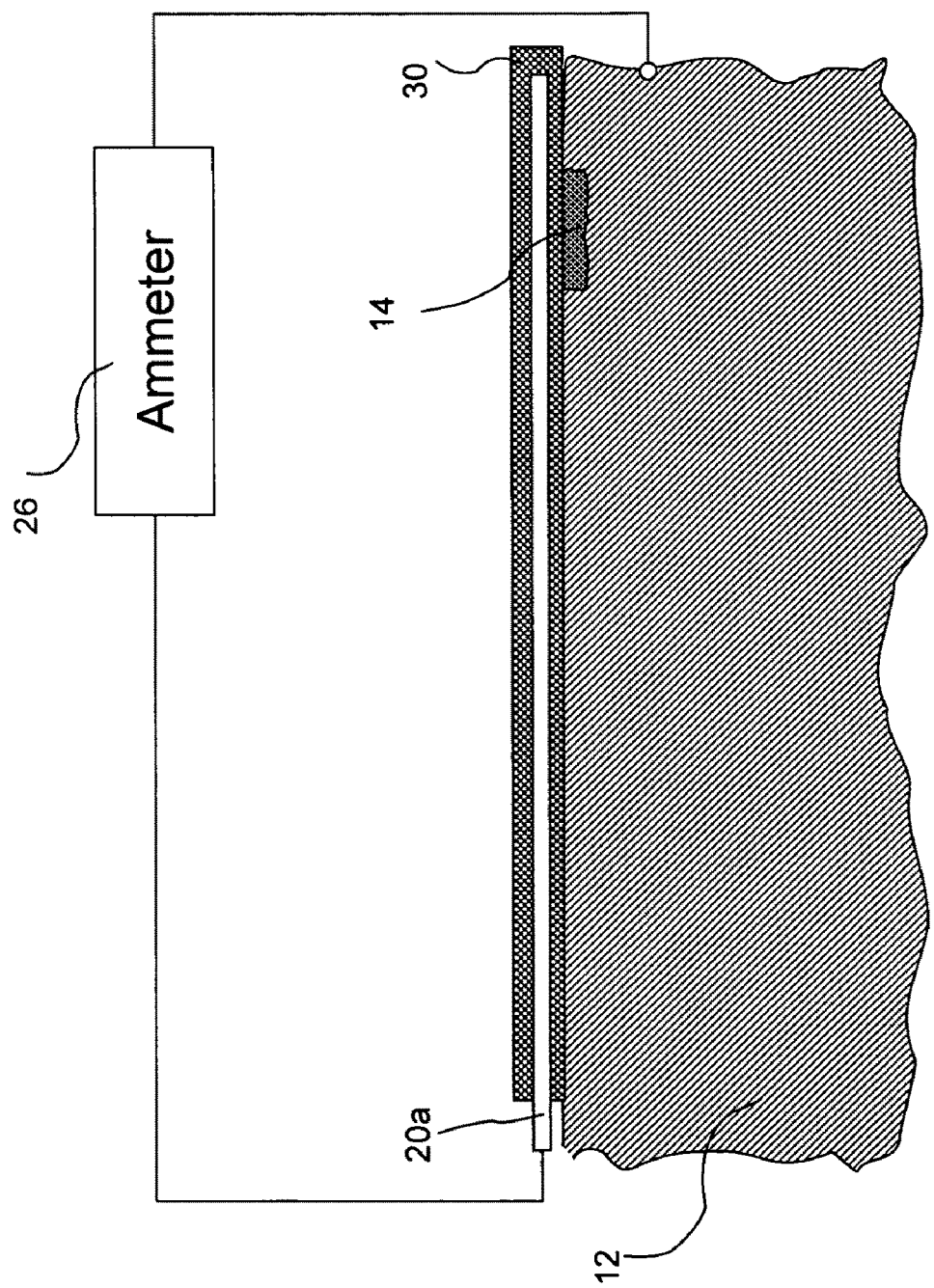
FIG. 12 illustrates a typical schematic diagram for the maximum oxidation power sensor with a long and thin noble electrode embedded under protective coatings for corrosion monitoring of undercoating corrosion over large areas.

FIG. 12 shows a schematic diagram for the maximum oxidation power sensor with a long and thin noble electrode (20*a*) embedded under protective coatings for corrosion monitoring of undercoating corrosion over large areas. The long and thin electrode may be made of wires, foil strips, or metal gauze.

Figure 13:
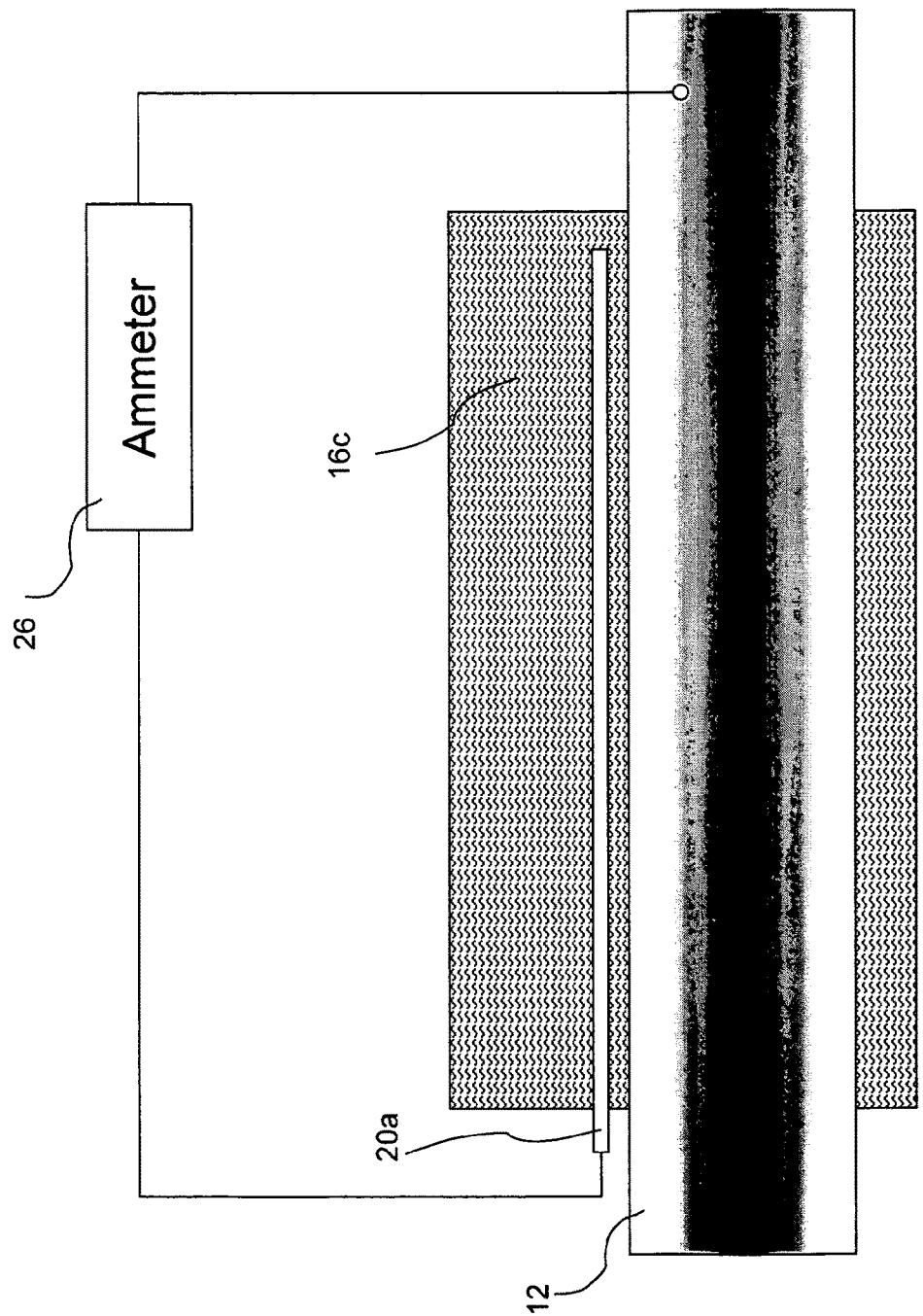
FIG. 13 illustrates a typical schematic diagram for maximum oxidation power sensor with a long and thin noble electrode embedded near the surface of a metal structure in concrete, soil or other electrolyte over large areas.
Figure 14:
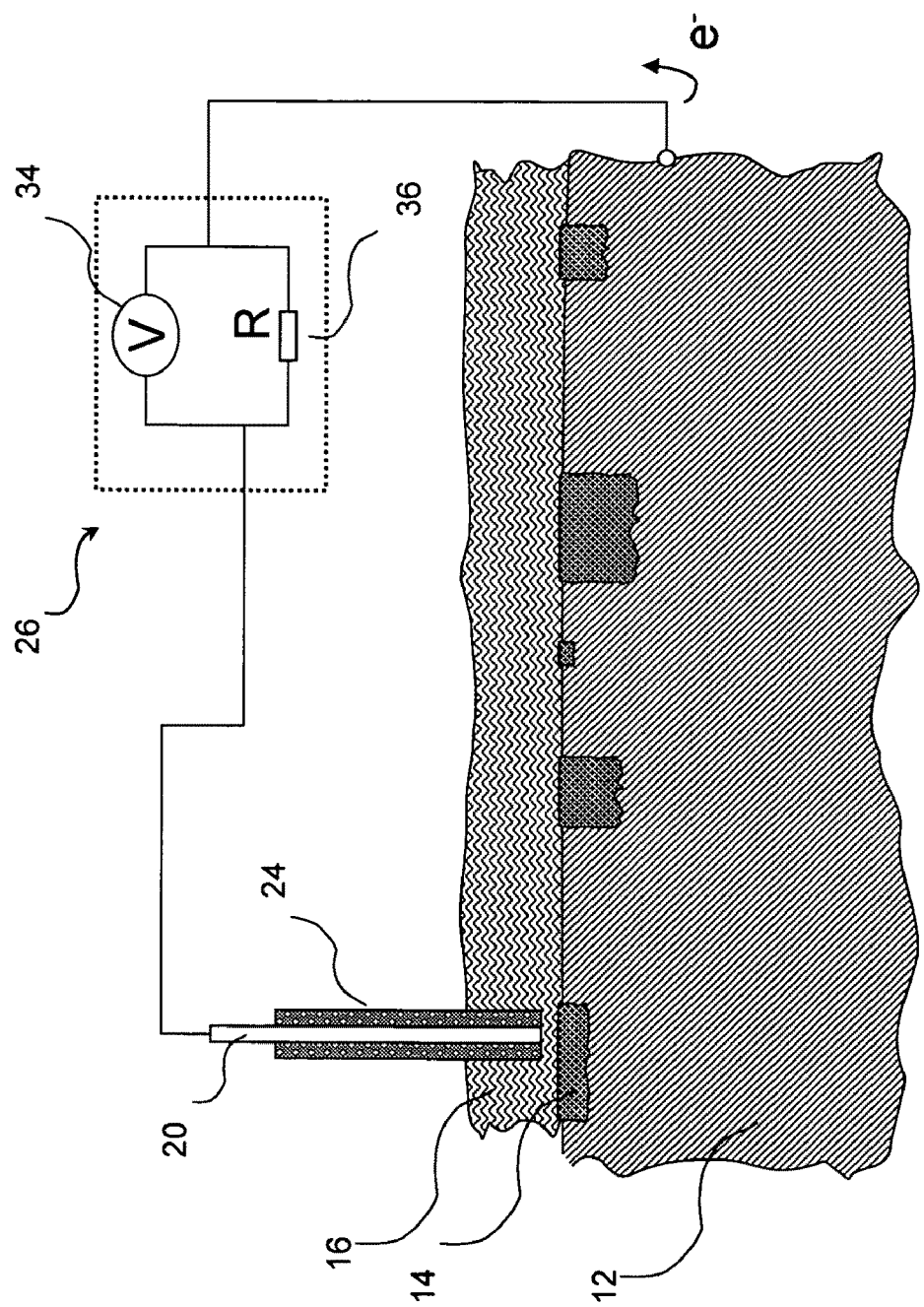
FIG. 14 illustrates that the current-measuring device can be made of a resistor and a voltmeter.

FIG. 13 shows the schematic diagram for the maximum oxidation power sensor with a long and thin noble electrode (20*a*) embedded near the surface of a metal structure, such as coated or uncoated pipes in concrete, soil, or other electrolytes (16*c*) over large areas. Any significant current indicated by the ammeter would indicate corrosion of the metal structure.
FIG. 14

FIG. 14 shows that the current-measuring device (26) described in the previous sections can be made of a resistor (36) and a voltmeter (34). As long as the resistor is small, the voltage produced by the resistor will be negligibly low for corrosion studies and measurements.
Example Results from Maximum Oxidation Power Sensors
FIGS. 15 and 16

Figure 15:
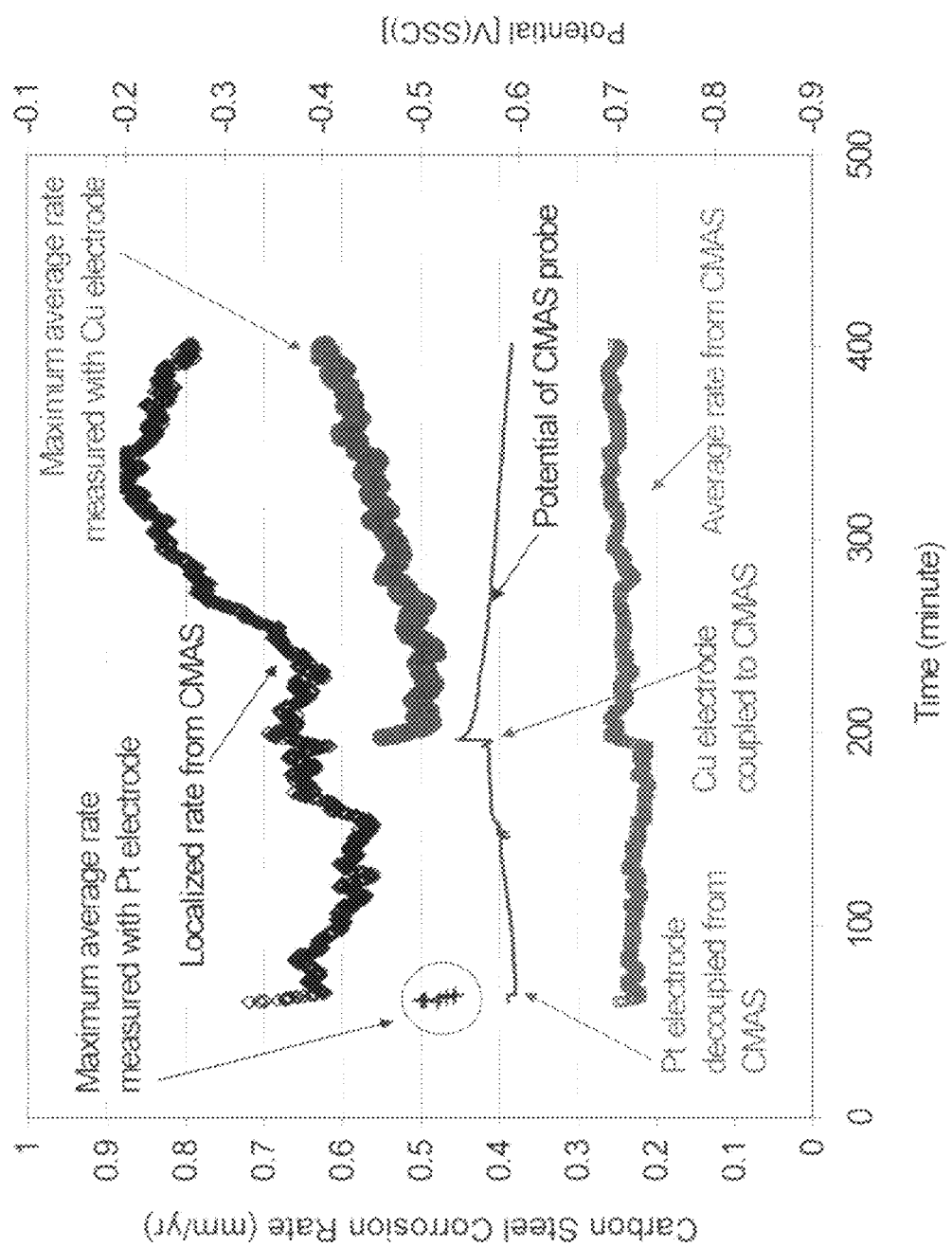
FIG. 15 illustrates a typical maximum average corrosion rate for carbon steel in bottled drinking water, obtained with maximum oxidation power corrosion sensors formed by a platinum or a copper noble electrode, the localized corrosion rate and the corrosion potential obtained with a coupled multielectrode array sensor (CMAS) for comparison.

FIG. 15 shows the typical maximum average corrosion rates for carbon steel in bottled drinking water (from Piney Wood Springs, Wood County, Tex., USA) obtained with the maximum oxidation power corrosion sensors formed by a platinum and a copper noble electrode. A coupled multielectrode array sensor (CMAS) (see U.S. Pat. No. 6,683,463 and L. Yang and N. Sridhar, "Coupled Multielectrode Online Corrosion Sensor," Materials Performance, 2003, September issue, page 48) was also used in the drinking water during the test. The CMAS probe had 14 carbon steel sensing electrodes, and they were connected (via the coupling joint) to the noble electrodes of the maximum oxidation power sensor during the measurements. The maximum average corrosion rates for carbon steel measured with both the copper oxidation sensor and the Pt oxidation power sensor varied from 0.5 to 0.6 mm/yr. To show the trend of the corrosivity, the localized corrosion rate and the average corrosion rate from the CMAS probe and the CMAS probe potential (the corrosion potential of the corroding metal) are also shown in FIG. 15. The localized corrosion rate varied from 0.5 to 0.8 mm/yr, and the average corrosion rate from the CMAS probe was about 0.2 mm/yr. If the average corrosion rate from a carbon steel CMAS probe can be used to estimate the general corrosion rate of carbon steel in the drinking water, the average corrosion rate from the CMAS probe should be bounded by the maximum average corrosion rate obtained from the oxidation power sensor, which is consistent with the results shown in FIG. 15. The corrosion potential was about −0.6 V [versus saturated silver/silver chloride (SSC) electrode], but increased slightly when it was coupled to the Cu electrode, suggesting that the Cu electrode surface area should be further reduced to not have any effect on the corrosion potential of the corroding metal.

Figure 16:
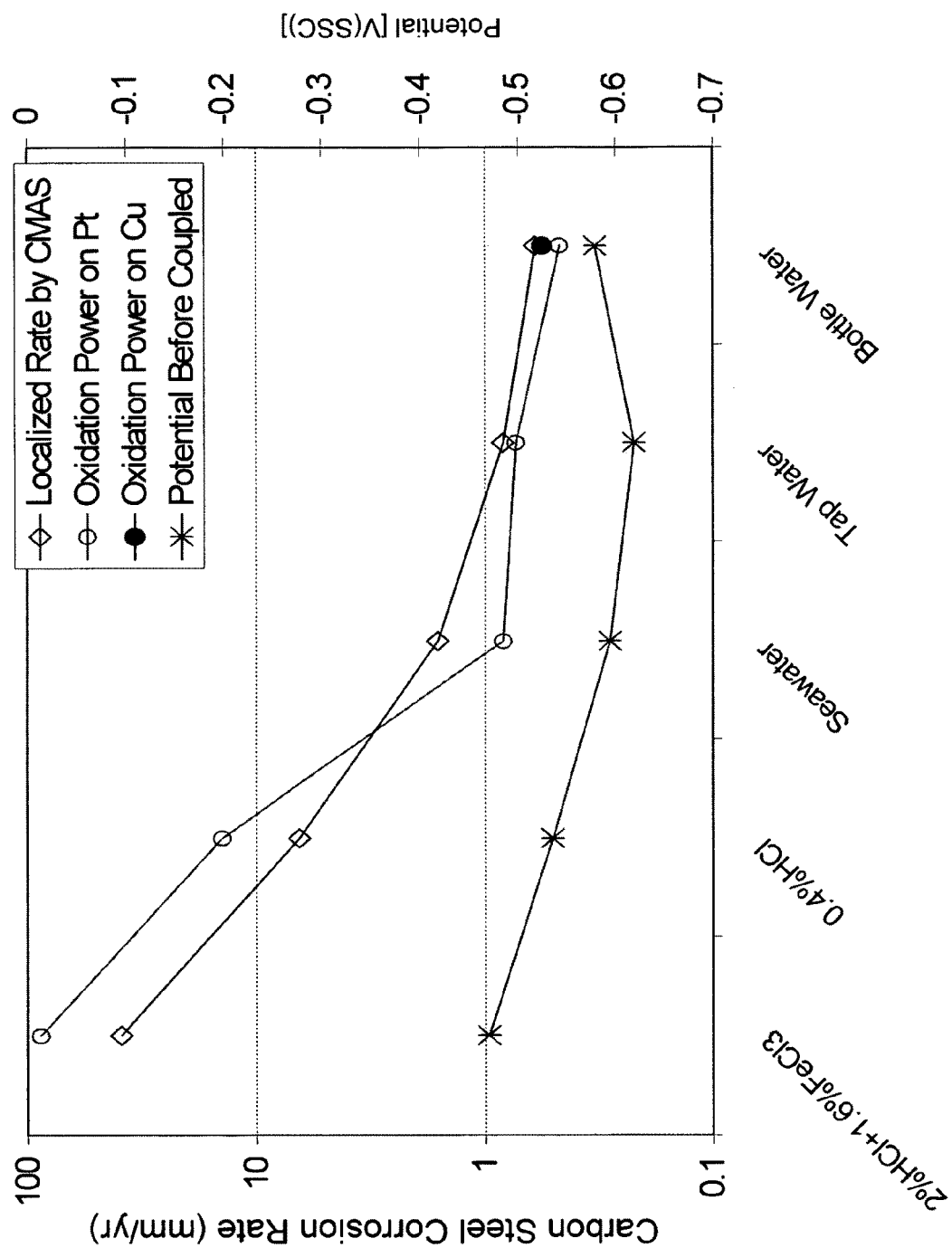
FIG. 16 illustrates a comparison of the maximum average corrosion rates obtained with the copper and the platinum maximum oxidation power sensors and the localized corrosion rates obtained with the CMAS probe for carbon steel.

FIG. 16 shows the comparison of the maximum average corrosion rates obtained with the copper and platinum maximum oxidation power sensors and the localized corrosion rates obtained with the CMAS probe for carbon steel. In general, the higher the localized corrosion rates were, the higher the maximum average corrosion rates measured with the oxidation power sensors were. FIG. 16 also shows that, in the cases with less corrosive medium (seawater, tap water and bottled water), the maximum average corrosion rate from the oxidation power sensors was lower than (did not bound) the localized corrosion rate from the CMAS probe. This is because the oxidation power sensor measures the maximum possible corrosion current, assuming the corrosion is taking place uniformly on the entire surface of the corroding metal, while localized corrosion is usually supported by the cathodic current, not only from the corroding section, but also from the other sections, especially the non-corroding sections (see discussion sections under FIGS. 1 and 2).

Figure 17:
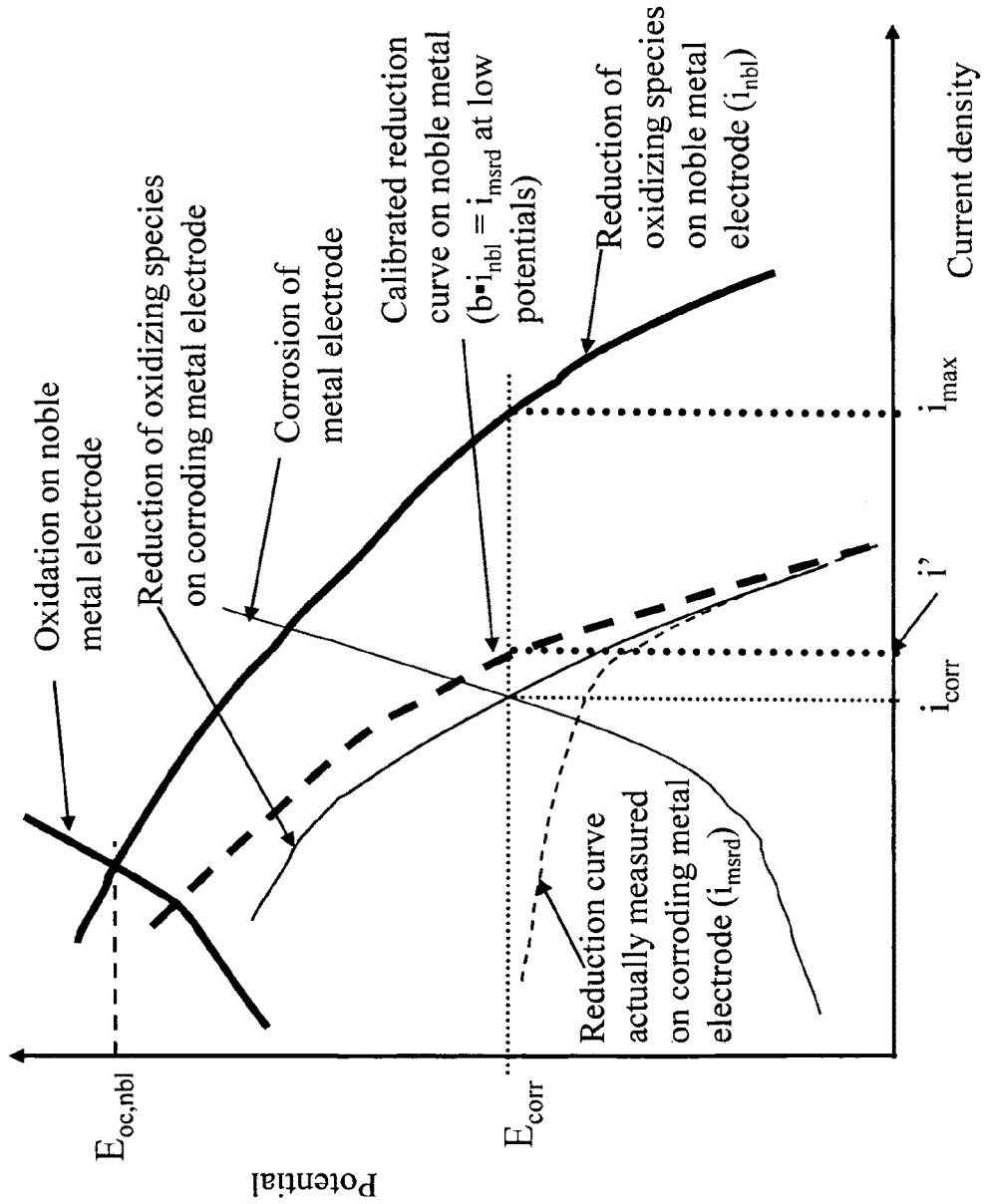
FIG. 17 illustrates the principle for calibrating the oxidation power corrosion sensors.

Oxidation Power Corrosion Sensor that can be Calibrated
FIG. 17

FIG. 17 shows the principle for calibrating the oxidation power corrosion sensors as discussed in the preceding sections, so that the maximum corrosion current density can be used to estimate the average rate of corrosion (usually the uniform corrosion rate) taking place on the corroding metal. In FIG. 17, the reduction current density curve on the noble electrode ($i_{nbl}$) is scaled down by a constant factor (b) so that the scaled curve (calibrated reduction curve or corrected reduction curve) meets the actually measured reduction curve on the corroding metal electrode ($i_{msrd}$) at low potentials:

$$b \cdot i_{nbl} = i_{msrd} \quad (1)$$

The average corrosion current density ($i_{corr}$), which usually corresponds to the uniform corrosion rate, may be estimated by the corrected current density from the oxidation power sensor (i')

Figure 18:
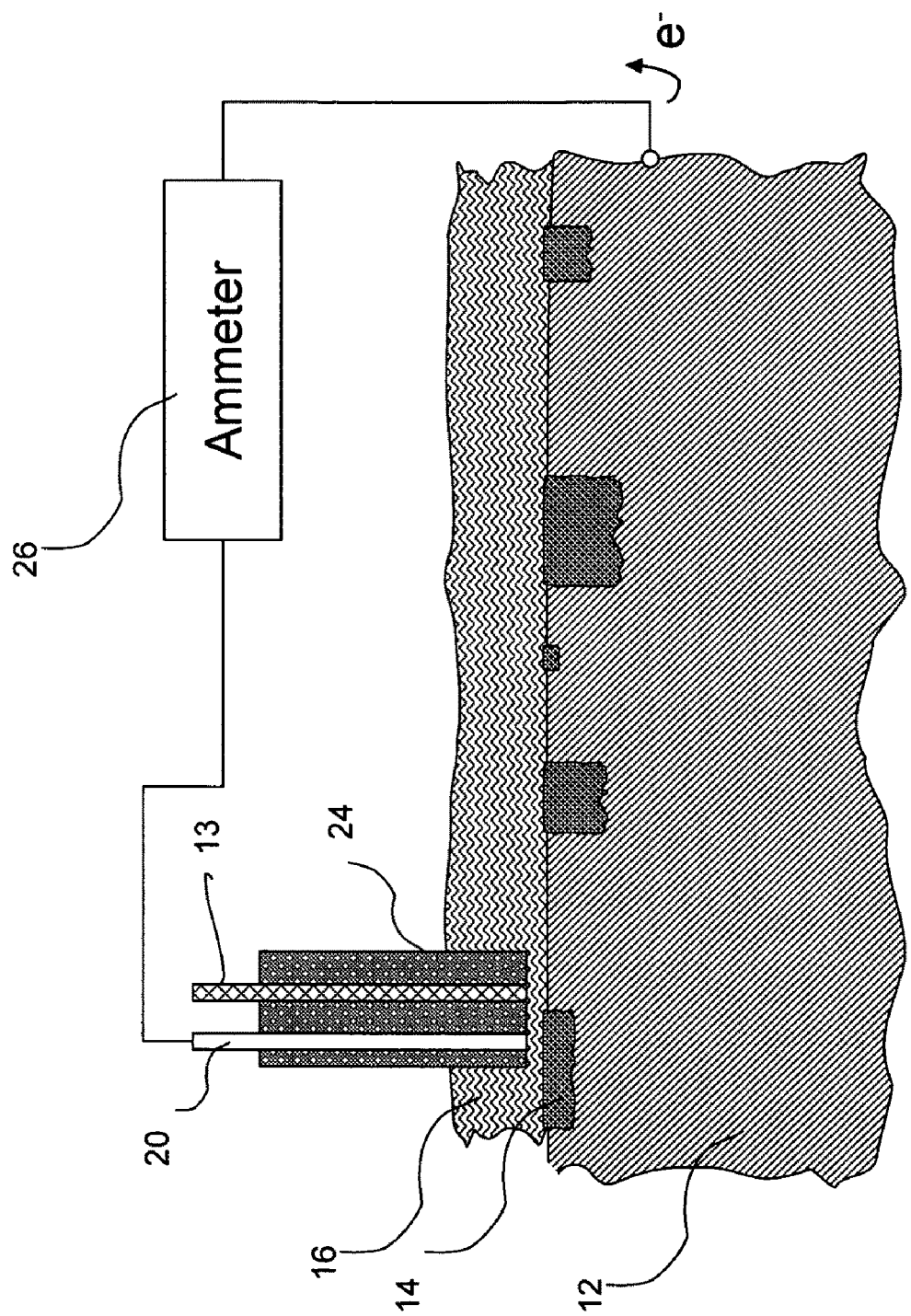
FIG. 18 illustrates the schematic diagram of a typical oxidation power corrosion sensor that may provide a calibrated corrosion rate.
Figure 19:
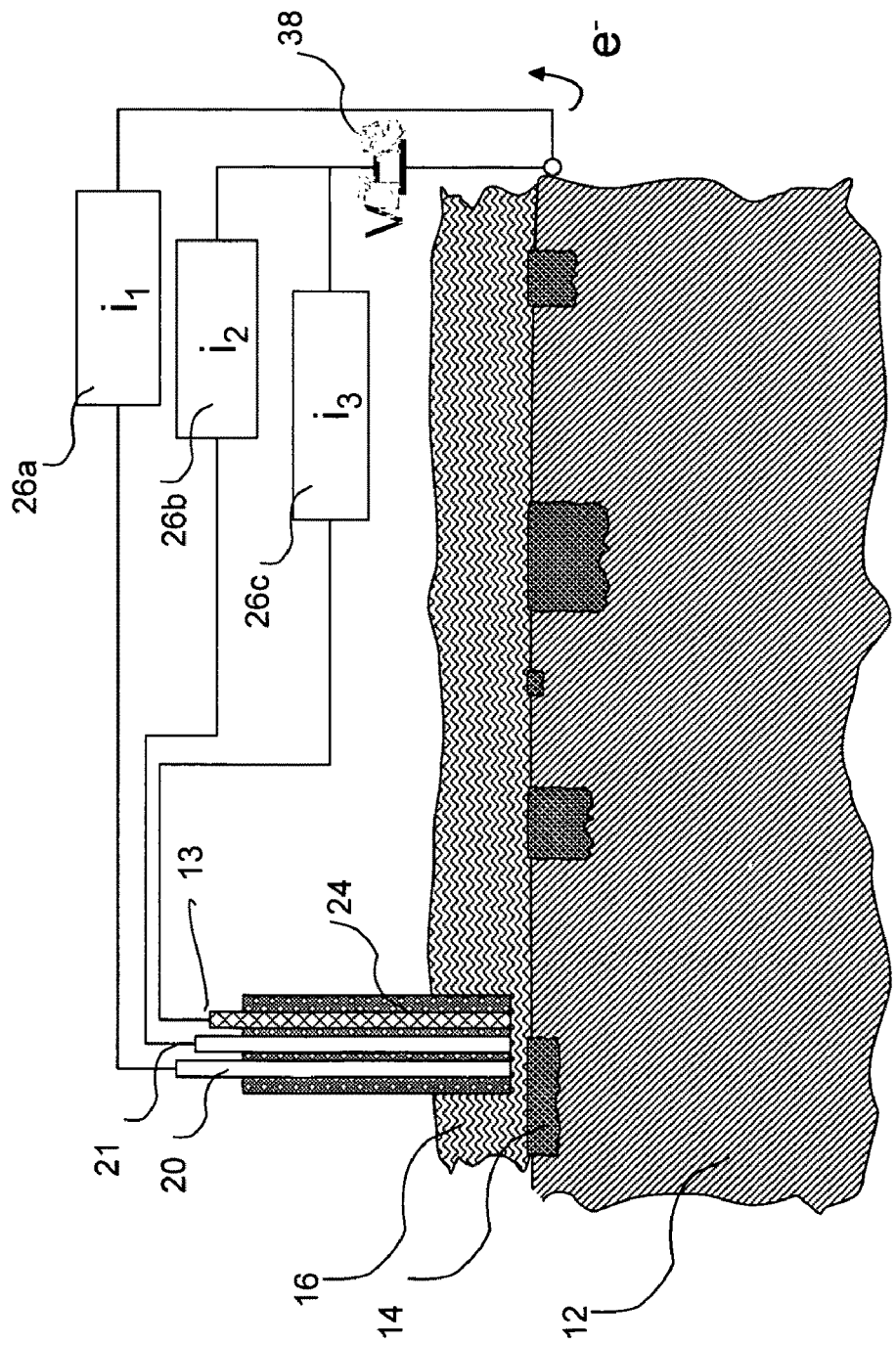
FIG. 19 illustrates the schematic diagram of an oxidation power corrosion sensor that has an additional corroding metal electrode and an additional noble metal electrode, both controlled at a potential lower than the corrosion potential, for the measurement of estimated corrosion rates.
Figure 20:
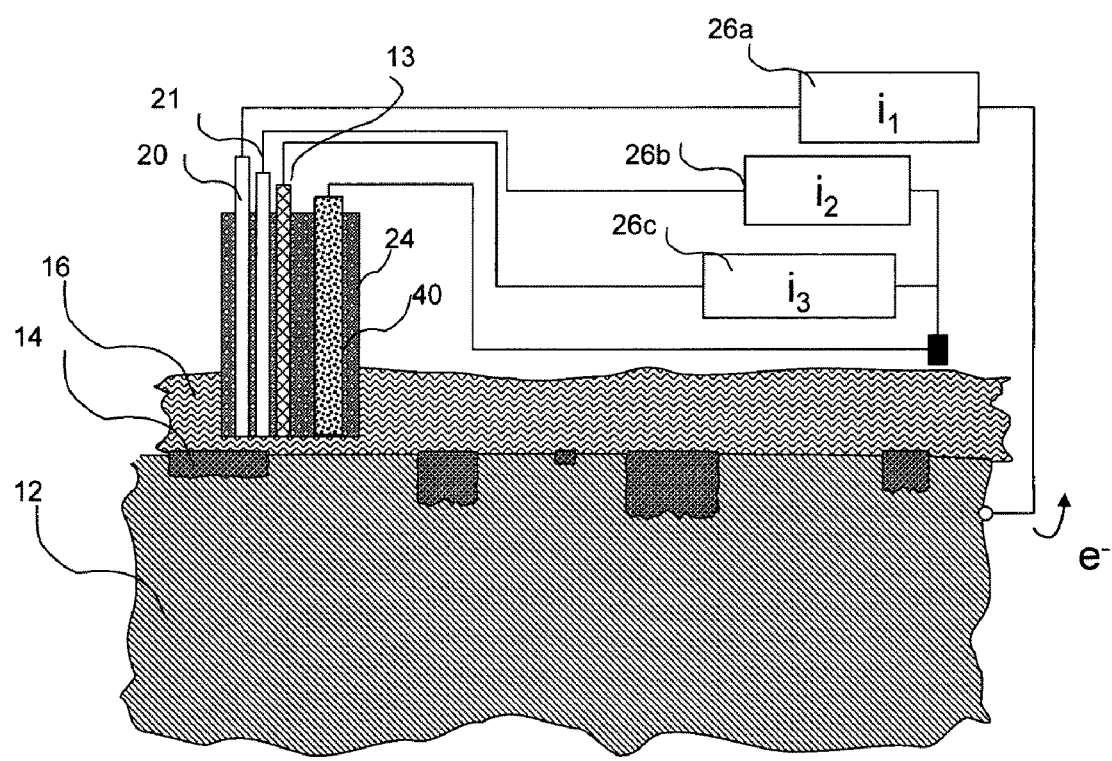
FIG. 20 illustrates the schematic diagram of an oxidation power corrosion sensor that has a sacrificial anode to lower the potential of the additional corroding metal electrode and the additional noble metal electrode for the measurement of estimated corrosion rates.

FIGS. 18, 19, and 20

FIG. 18 shows the schematic diagram of an oxidation power corrosion sensor that may provide calibrated corrosion rates. FIG. 18 has an additional electrode (13) made of the corroding metal material, and this corroding metal electrode can be polarized (e.g., with a separate potentiostat) for measuring the reduction curve of the corroding metal. This reduction curve may be used to calibrate the reduction curve from the noble electrode, as discussed under FIG. 17.

FIG. 19 shows the schematic diagram of an oxidation power corrosion sensor that has an additional (second) corroding metal electrode (13) and an additional (second) noble metal electrode (21) for the measurements of estimated corrosion rates. The two additional electrodes are controlled at a potential that is significantly lower than the corrosion potential of the corroding metal, with a voltage source (38). Three current-measuring devices (26a, 26b and 26c) are used to measure the currents from the first and second noble electrodes ($i_1$ and $i_2$), respectively, and the current to the second corroding metal electrode ($i_3$). Under this condition, the actually measured cathodic current from the second corroding metal electrode ($i_3$) is not affected by the corrosion current, because the corrosion current on the corroding metal equals zero at this potential. Thus, the corrosion current density may be estimated by ($i_1 i_3 / i_2$) where $i_1$ is the maximum reduction current density measured on the noble electrode at the corrosion potential ($i_{max}$ as shown in FIGS. 2 and 17). The value of ($i_1 i_3 / i_2$) is the corrected current density from the oxidation power sensor (i' as shown in FIG. 17) and the ratio of $i_3/i_2$ is the b value in Equation (1) at the potential of V (versus the corrosion potential of the corroding metal).

FIG. 20 is the same as FIG. 19, except that it has a sacrificial anode (40) to lower the potentials of the two secondary electrodes. This anode avoids the use of a battery or a power supplier connected to these secondary electrodes, which greatly simplifies the operations of the sensor for field applications. The absence of the power supply also reduces the electrical noises during the measurements. The type and the surface area of the sacrificial anode should be selected based on its electrochemical polarization curve and based on testing results, so that it lowers the potential of the two secondary electrodes to such a potential that the corrosion current on the second corroding metal electrode just diminishes to a near zero-value. In FIG. 20, the sacrificial anode is built into a sensor, as shown in the figure, but it can also be placed apart from the sensor.

Figure 21:
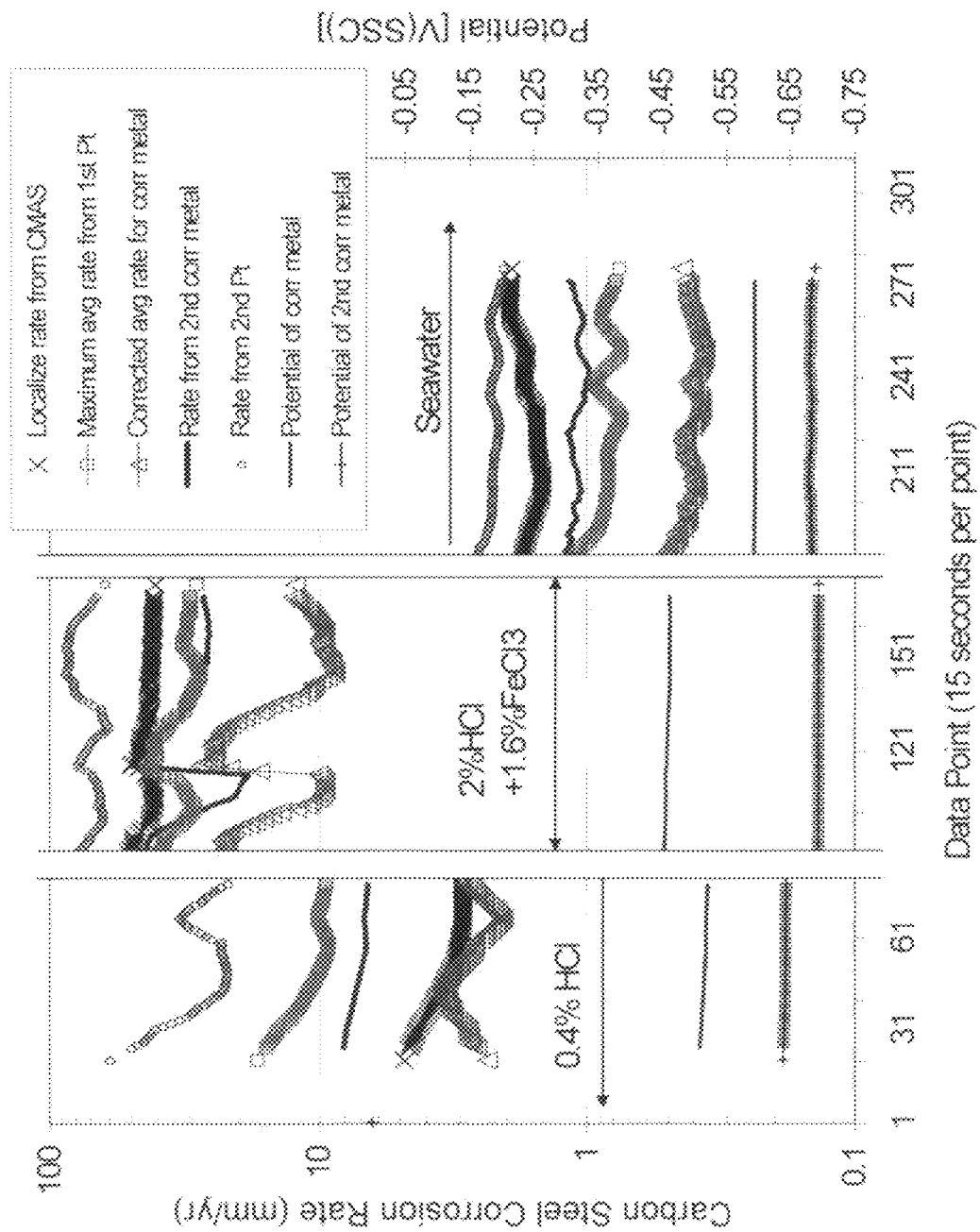
FIG. 21 illustrates the corrected average corrosion rate from a calibrated oxidation power sensor and the comparison with the localized corrosion rate from a carbon steel CMAS probe in different solutions.

Example Results from Calibrated Oxidation Power Sensors
FIG. 21

FIG. 21 illustrates the corrected average corrosion rate from a calibrated oxidation power sensor and the comparison with the localized corrosion rate from a CMAS probe in different solutions. The corroding metal was low carbon steel and the noble metal was platinum. The sacrificial anode was an aluminum (Type1100) wire placed in the same solution. The other parameters, also shown in the figure, include the maximum average corrosion rate from the first Pt electrode (corresponding to $i_{max}$ in FIG. 17), the rate from the second Pt electrode (corresponding to $i_2$ in FIG. 20) and the rate from the second corroding metal electrode (corresponding to $i_3$ in FIG. 20). In addition, the potentials of the two corroding metals are also shown in the figure. The difference between the two potentials was between 90 and 130 mV, so that the corroding current on the second corroding metal electrode is expected to be near zero and the measured current density from the second corroding meal equals the cathodic current density. It should be mentioned that the potentials shown in FIG. 21 are not required during corrosion monitoring, as long as it has been demonstrated/verified that the sacrificial anode has the ability to produce the appropriate potential (not too high, which cannot eliminate the corrosion current effect; and not to low, which causes other oxidizing species that are normally stable at the corrosion potential to react and to contribute to the reduction current density).

The corrected average corrosion rates for carbon steel are 3, 15, and 0.3 mm/yr in 0.4% HCl solution, 2% HCl+1.6FeCl$_3$ solution, and seawater, respectively. The value obtained from the seawater is very close to the literature-reported general corrosion rate of carbon steel measured in seawater.

Advantages:

The oxidation power sensor for corrosion monitoring has the following advantages:

Low Cost: The maximum oxidation power sensor is simple and requires only an ammeter and a noble electrode when used to measure the bounding corrosion rate of a metal structure.

Measuring Corrosion Rate of Actual System Components: The maximum oxidation power sensor measures the maximum average (or uniform) corrosion rate of system components, rather than the corrosion rate of a coupon.

Sensing Electrode Not Consumable: The sensing electrode in a maximum oxidation power sensor is a noble electrode, and it does not corrode under the monitoring conditions. There is no need to change or replace the sensing electrode.

Non Destructive or No Disturbance to System Components under Testing: The noble electrode in an oxidation power corrosion sensor is small in surface area and can be directly coupled to large system components. This arrangement does not require polarizations to the system components; it causes no perturbations to the system component corrosion conditions.

Wide Applications: The sensors can be used to measure or detect corrosion under coatings, in soil or concrete.

Corrosion Rates Derived from the Oxidation Reaction on the Noble Electrode Can Be Easily Calibrated to Closely Represent the True Average or Uniform Corrosion Rate: By comparing the cathodic current density from the noble metal electrode (or a separate noble metal electrode) with the cathodic current density of the corroding metal electrode (an electrode made of the same material as the corroding metal to be measured) at a potential significantly below the corrosion potential, the current density measured from the noble electrode at the corrosion potential can be calibrated to a value that is close to the true average or uniform corrosion rate of the corroding metal.

Other Embodiments

Although the present invention has been described in detail, it should be understood that various changes, substitutions, and alterations can be made hereto, without departing from the spirit and scope of the invention as defined by the appended claims.

The invention claimed is:

1. A method to form an oxidation power sensor for monitoring corrosion of a corroding metal in a corrosion environment, comprising the steps of:
    a) Placing a corrosion-resistant electrode next to a surface of the corroding metal to be monitored, whereby there is an ionic conducting path between the corrosion-resistant electrode and the corroding metal via an electrolyte, wherein placing the corrosion-resistant electrode comprises selecting a material of the corrosion-resistant electrode such that the corrosion-resistant electrode is more catalytically active for cathodic reactions than the corroding metal such that a cathodic current density of the corrosion-resistant electrode defines a bounding average corrosion current density for the corroding metal;
    b) Controlling the potential of the corrosion-resistant electrode to be substantially equal to a corrosion potential of the corroding metal;
    c) Measuring a cathodic current from the corrosion-resistant electrode; and
    d) Using the cathodic current from the corrosion-resistant electrode to detect corrosion or to derive a uniform corrosion rate of the corroding metal.

2. The method of claim 1, wherein the corrosion-resistant electrode is movable on the surface of the corroding metal to detect the location of corrosion over an area.

3. The method of claim 1, wherein the ionic conducting path is formed by a confined volume of the electrolyte that comprises one of a soaked sponge, a soaked piece of fibre, a solid electrolyte, and a stream of water flow.

4. The method of claim 1, wherein the corroding metal is covered by a coating and the corrosion of the corroding metal is under the coating.

5. The method of claim 1, wherein the corrosion-resistant electrode comprises a thin metal wire or gauze placed next to the corroding metal for monitoring corrosion over an area.

6. The method of claim 5, wherein the corroding metal is painted or embedded in soil or concrete.

7. The method of claim 6, wherein the corrosion-resistant electrode is imbedded in the paint, soil or concrete.

8. The method of claim 1, wherein the potential of the corrosion-resistant electrode is controlled via a separate counter electrode.

9. The method of claim 1, wherein the potential of the corrosion-resistant electrode is controlled by coupling it to the corroding metal through a current-measuring device.

10. The method of claim 1, wherein the corroding metal is a stand-alone corroding metal electrode made from a material that is the same as a material from which the corroding metal is made.

11. The method of claim 10, wherein the corroding metal electrode is incorporated into a body with the corrosion-resistant electrode to form an oxidation power sensor.

12. A method to form an oxidation power sensor for monitoring corrosion of a corroding metal in a corrosion environment, comprising the steps of:
    a) Placing a corrosion-resistant electrode next to a surface of the corroding metal to be monitored, whereby there is an ionic conducting path between the corrosion-resistant electrode and the corroding metal via an electrolyte, wherein placing the corrosion-resistant electrode comprises selecting a material of the corrosion-resistant electrode such that the corrosion-resistant electrode is more catalytically active for cathodic reactions than the corroding metal such that a cathodic current density of the corrosion-resistant electrode defines a bounding average corrosion current density for the corroding metal;
    b) Controlling the potential of the corrosion-resistant electrode to be substantially equal to a corrosion potential of the corroding metal;
    c) Measuring a cathodic current from the corrosion-resistant electrode controlled at the controlled potential;
    d) Measuring the cathodic currents for the corroding metal and for the corrosion-resistant electrode at a potential that is at least 30 mV more negative than the corrosion potential of the corroding metal;
    e) Correcting the cathodic current from the corrosion-resistant electrode measured at the controlled potential according to the cathodic currents measured for the corroding metal and for the corrosion-resistant electrode at the more negative potential; and
    f) Using the corrected cathodic current to estimate a uniform corrosion rate of the corroding metal.

13. The method of claim 12, wherein the cathodic current for the corroding metal at the more negative potential is measured from a separate corroding metal electrode made of a material that is the same as the corroding metal.

14. The method of claim 12, wherein the cathodic current for the corrosion-resistant electrode at the more negative potential is measured from a separate corrosion-resistant electrode made of a material that is the same as the corrosion-resistant electrode.

15. The method of claim 12, wherein the more negative potential is obtained using a sacrificial anode.

16. The method of claim 15, wherein the sacrificial anode is incorporated into a body with the corrosion-resistant electrode to form an oxidation power sensor that is calibrated for estimation of the uniform corrosion rate of the corroding metal.

* * * * *